US006794493B2

(12) United States Patent
Walston et al.

(10) Patent No.: US 6,794,493 B2
(45) Date of Patent: Sep. 21, 2004

(54) ANTITHROMBIN H-HELIX MUTANTS

(75) Inventors: Timothy Walston, Fitchburg, WI (US); Scott Cooper, Holmen, WI (US); Alireza Rezaie, Eureka, MO (US)

(73) Assignee: WiSys Technology Foundation, Inc., Madison, WI (US)

( * ) Notice: Subject to any disclaimer, the term of this patent is extended or adjusted under 35 U.S.C. 154(b) by 496 days.

(21) Appl. No.: 09/828,592

(22) Filed: Apr. 6, 2001

(65) Prior Publication Data

US 2001/0055591 A1 Dec. 27, 2001

Related U.S. Application Data

(60) Provisional application No. 60/195,872, filed on Apr. 7, 2000.

(51) Int. Cl.[7] ........................ A61K 35/14; A61K 38/00; C07K 1/00; C07K 14/00; C07K 16/00

(52) U.S. Cl. ....................... 530/381; 530/384; 530/350; 435/13; 424/94.64

(58) Field of Search ........................... 424/94.64, 225.1, 424/94.63; 435/212, 91.1, 325, 13; 530/350, 384, 381

(56) References Cited

FOREIGN PATENT DOCUMENTS

WO WO 0071714 11/2000

OTHER PUBLICATIONS

Ahn, Sang Hoon, Naturally Occuring Mutations Near Precore Translational Initiation Site Reduce Hepatitis B E Antigen Production. Hepatology, (Oct., 2002) vol. 36. No. 4 Part 2, p. 370A.*

Rebecca Shirk, Role of the H Helix in Heparin binding to Protein C Inhibitor (Journal of Biological Chemistry, vol. 269. No. 46. pp. 28690–28695).*

Joeph Emmerich, A Phenyllalanine 402 to Leucine Mutation is Responsible for A Stable Inactive Conformation of Antithrombin Thrombosis Research, 1994 vol. 76, No. 3, pp. 305–315.*

Henry Jakubowski, Bovine Lung Thrombomodulin (Journal of Biological Chemistry, vol. 262. No. 8. pp. 3876–3882).*

Turecek, P.L., H. Gritsch, G. Richter, W. Auer, L. Pichler, H.P. Schwarz. Assessment of bleeding for the evaluation of therapeutic preparations in small animal models of antibody–induced hemophilia and von willebrand disease. Thromb Haemostas. Mar. 1997. 77(3):591–9.

Wu, H., Reading, J. Qian, D.K. Okita, E. Parker, P. Lollar, L.W. Hoyer, BM. Conti–Fine. Mechanism of the immune response to human factor VIII in muring hemophilia A. Thromb Haemost. Jan. 2001. 85(1):125–33.

* cited by examiner

*Primary Examiner*—Robert A. Wax
*Assistant Examiner*—Robert B. Mondesi
(74) *Attorney, Agent, or Firm*—Godfrey & Kahn, S.C.

(57) ABSTRACT

Mutant antithrombin modified to carry a more positive charge in the H-helix is provided. The modified antithrombin modulates the activities of thrombin, and extends the bioavailability of factor VIII.

15 Claims, 3 Drawing Sheets

Template curve of heparin accelerated thrombin inhibiton by AT.

FIG.2 SUBCLONING STRATEGY TO GENERATE REECOMBINANT ANTITHROMBIN WITH H-HELIX AND REACTIVE SITE LOOP MUTANTS.
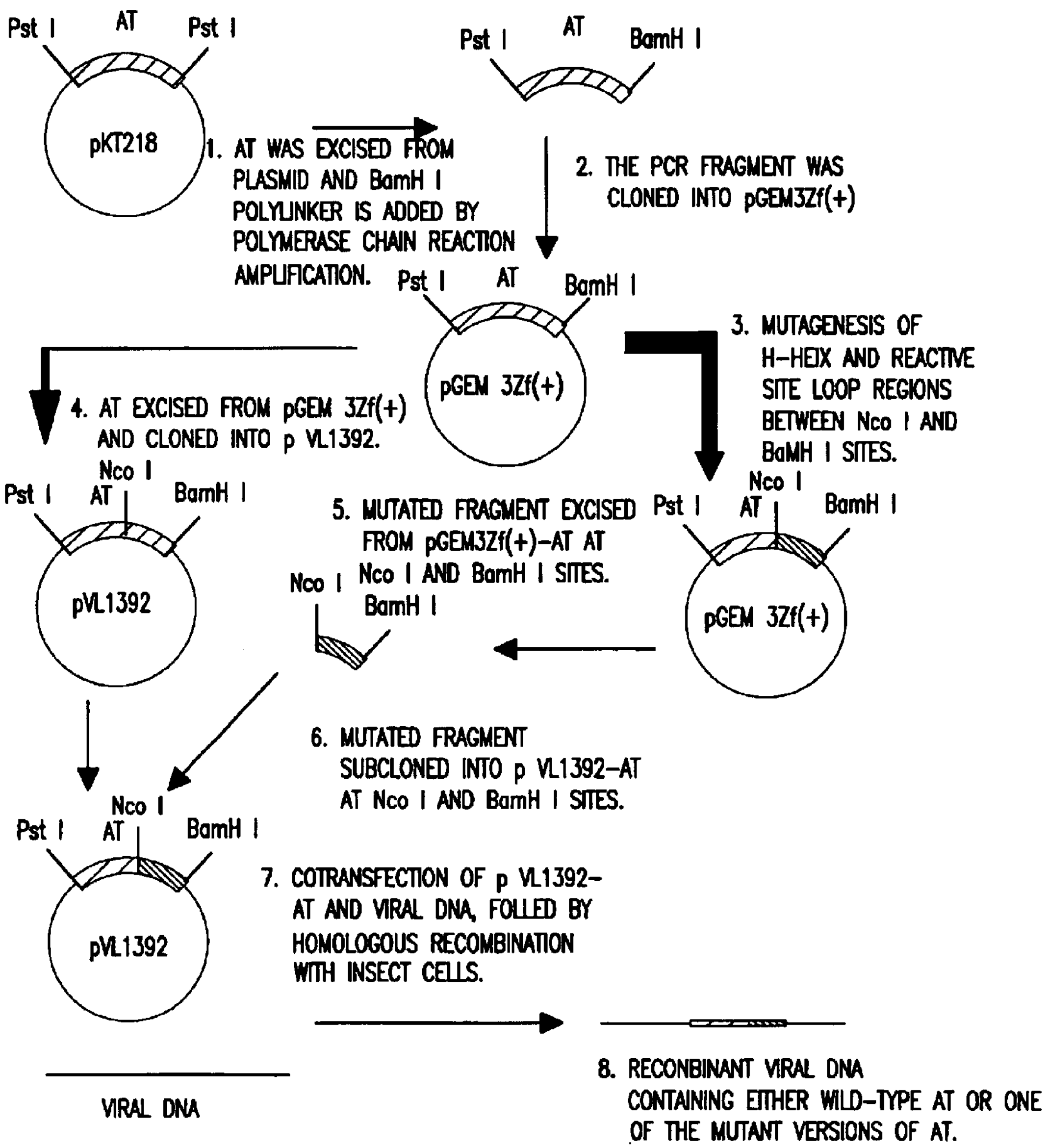

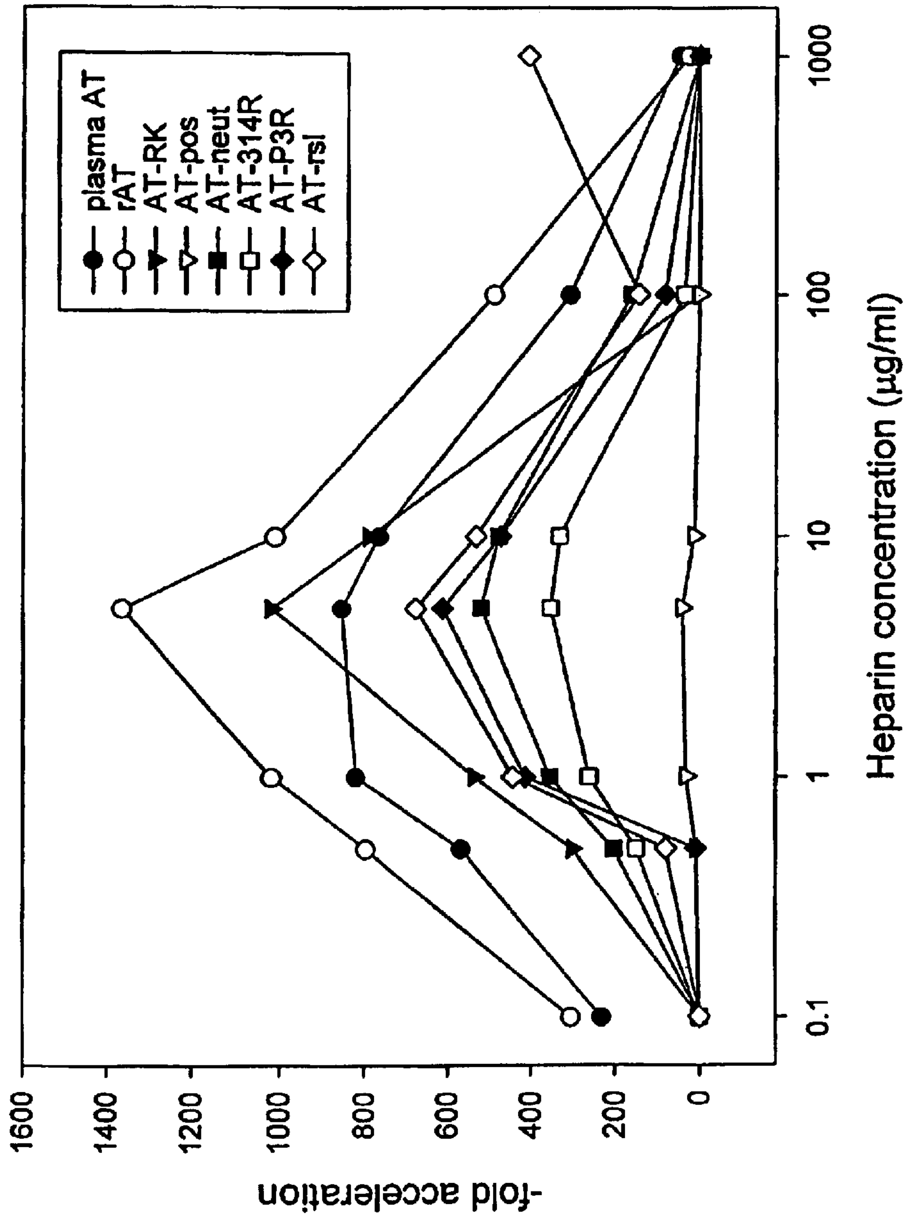
FIG. 3 Template curve of heparin accelerated thrombin inhibiton by AT.

SEQUENCE LISTING

```
<160> NUMBER OF SEQ ID NOS: 16

<210> SEQ ID NO 1
<211> LENGTH: 33
<212> TYPE: DNA
<213> ORGANISM: Homo sapiens

<400> SEQUENCE: 1

ccagaggtgc tgcggaagtg gctggatgaa ttg                                  33


<210> SEQ ID NO 2
<211> LENGTH: 42
<212> TYPE: DNA
<213> ORGANISM: Homo sapiens

<400> SEQUENCE: 2

gagtggctga aaaaattgaa gaagatgatg ctggtggttc ac                        42


<210> SEQ ID NO 3
<211> LENGTH: 42
<212> TYPE: DNA
<213> ORGANISM: Homo sapiens

<400> SEQUENCE: 3

gagtggctgg ctgcattggc ggcgatgatg ctggtggttc ac                        42


<210> SEQ ID NO 4
<211> LENGTH: 30
<212> TYPE: DNA
<213> ORGANISM: Homo sapiens

<400> SEQUENCE: 4

gaattggagg agaggatgct ggtggttcac                                      30


<210> SEQ ID NO 5
<211> LENGTH: 45
<212> TYPE: DNA
<213> ORGANISM: Homo sapiens

<400> SEQUENCE: 5

gctgttgtga ttasattccg ttcggcaaga cccaacaggg tgact                     45


<210> SEQ ID NO 6
<211> LENGTH: 1395
<212> TYPE: DNA
```

-continued

<213> ORGANISM: Homo sapiens

<400> SEQUENCE: 6

```
atgtattcca atgtgatagg aactgtaacc tctggaaaaa ggaaggttta tcttttgtcc     60
ttgctgctca ttggcttctg ggactgcgtg acctgtcacg ggagccctgt ggacatctgc    120
acagccaagc cgcgggacat tcccatgaat cccatgtgca tttaccgctc cccggagaag    180
aaggcaactg aggatgaggg ctcagaacag aagatcccgg aggccaccaa ccggcgtgtc    240
tgggaactgt ccaaggccaa ttcccgcttt gctaccactt tctatcagca cctggcagat    300
tccaagaatg acaatgataa cattttcctg tcacccctga gtatctccac ggcttttgct    360
atgaccaagc tgggtgcctg taatgacacc ctccagcaac tgatggaggt atttaagttt    420
gacaccatat ctgagaaaac atctgatcag atccacttct tctttgccaa actgaactgc    480
cgactctatc gaaaagccaa caaatcctcc aagttagtat cagccaatcg cctttttgga    540
gacaaatccc ttaccttcaa tgagacctac caggacatca gtgagttggt atatggagcc    600
aagctccagc ccctggactt caaggaaaat gcagagcaat ccagagcggc catcaacaaa    660
tgggtgtcca ataagaccga aggccgaatc accgatgtca ttccctcgga agccatcaat    720
gagctcactg ttctggtgct ggttaacacc atttacttca agggcctgtg gaagtcaaag    780
ttcagccctg agaacacaag gaaggaactg ttctacaagg ctgatggaga gtcgtgttca    840
gcatctatga tgtaccagga aggcaagttc cgttatcggc gcgtggctga aggcacccag    900
gtgcttgagt tgcccttcaa aggtgatgac atcaccatgg tcctcatctt gcccaagcct    960
gagaagagcc tggccaaggt ggagaaggaa ctcaccccag aggtgctgca ggagtggctg   1020
gatgaattgg aggagatgat gctggtggtc cacatgcccc gcttccgcat tgaggacggc   1080
ttcagtttga aggagcagct gcaagacatg ggccttgtcg atctgttcag ccctgaaaag   1140
tccaaactcc caggtattgt tgcagaaggc cgagatgacc tctatgtctc agatgcattc   1200
cataaggcat ttcttgaggt aaatgaagaa ggcagtgaag cagctgcaag taccgctgtt   1260
gtgattgctg gccgttcgct aaaccccaac agggtgactt tcaaggccaa caggcctttc   1320
ctggttttta taagagaagt tcctctgaac actattatct tcatgggcag agtagccaac   1380
ccttgtgtta agtaa                                                    1395
```

<210> SEQ ID NO 7
<211> LENGTH: 11
<212> TYPE: PRT
<213> ORGANISM: Homo sapiens

<400> SEQUENCE: 7

```
Leu Arg Lys Trp Leu Lys Met Phe Lys Lys Arg
  1               5                  10
```

<210> SEQ ID NO 8
<211> LENGTH: 11
<212> TYPE: PRT
<213> ORGANISM: Homo sapiens

<400> SEQUENCE: 8

```
Leu Gln Glu Trp Leu Asp Glu Leu Glu Glu Met
  1               5                  10
```

<210> SEQ ID NO 9
<211> LENGTH: 11
<212> TYPE: PRT
<213> ORGANISM: Homo sapiens

-continued

<400> SEQUENCE: 9

Leu Arg Lys Trp Leu Asp Glu Leu Glu Glu Met
1 5 10

<210> SEQ ID NO 10
<211> LENGTH: 11
<212> TYPE: PRT
<213> ORGANISM: Homo sapiens

<400> SEQUENCE: 10

Leu Gln Glu Trp Leu Lys Lys Leu Lys Lys Met
1 5 10

<210> SEQ ID NO 11
<211> LENGTH: 11
<212> TYPE: PRT
<213> ORGANISM: Homo sapiens

<400> SEQUENCE: 11

Leu Gln Glu Trp Leu Asn Gln Leu Gln Gln Met
1 5 10

<210> SEQ ID NO 12
<211> LENGTH: 11
<212> TYPE: PRT
<213> ORGANISM: Homo sapiens

<400> SEQUENCE: 12

Leu Gln Glu Trp Leu Asp Glu Leu Glu Glu Arg
1 5 10

<210> SEQ ID NO 13
<211> LENGTH: 8
<212> TYPE: PRT
<213> ORGANISM: Homo sapiens

<400> SEQUENCE: 13

Phe Thr Phe Arg Ser Ala Arg Leu
1 5

<210> SEQ ID NO 14
<211> LENGTH: 8
<212> TYPE: PRT
<213> ORGANISM: Homo sapiens

<400> SEQUENCE: 14

Ile Ala Gly Arg Ser Leu Asn Pro
1 5

<210> SEQ ID NO 15
<211> LENGTH: 8
<212> TYPE: PRT
<213> ORGANISM: Homo sapiens

<400> SEQUENCE: 15

Ile Thr Phe Arg Ser Ala Arg Pro
1 5

-continued

```
<210> SEQ ID NO 16
<211> LENGTH: 8
<212> TYPE: PRT
<213> ORGANISM: Homo sapiens

<400> SEQUENCE: 16

Ile Arg Phe Arg Ser Ala Arg Pro
  1               5
```

ANTITHROMBIN H-HELIX MUTANTS

PRIORITY

This application claims priority to U.S. Provisional application 60/195,872 filed Apr. 7, 2000.

FIELD OF THE INVENTION

This invention relates to factors involved in the coagulation pathway, and more particularly to serpins modified to selectively modulate the coagulation pathway.

BACKGROUND OF THE INVENTION

The regulation of blood clotting is an important process in animals with a developed cardiovascular system. Clotting is achieved through either an intrinsic or extrinsic pathway that involves a cascade of protein activations resulting in the conversion of soluble fibrinogen to insoluble fibrin.

The intrinsic pathway includes the following steps: (1) factor XII is activated; (2) activated factor XII activates factor XI; (3) activated factor XI activates factor IX; (4) activated factor IX, with interaction from activated factor VIII, activates factor X; (5) activated factor X converts prothrombin to thrombin in the presence of activated factor V; (6) thrombin cleaves fibrinogen to fibrin; (7) fibrin polymerizes to form fibrin strands.

The extrinsic pathway includes the following steps: (1) trauma to the vessel wall causes binding of factor VII in plasma to tissue factor present in non-vascular tissue cells; (2) factor VII is activated; (3) factor VII-tissue factor complex activates Factor X. The remaining steps are the same as steps 5–7 of the intrinsic pathway.

A fine line must be maintained between the activation and inactivation of coagulation (Gaffney et al., 1999). If clotting proteins are constantly inactivated, then blood loses the ability to clot which could lead to life-threatening bleeding events.

Hemophilia A is an inherited factor VIII deficiency that results in extensive bleeding after trauma and may involve spontaneous bleeding into joints and muscles. In normal individuals, factor VIII circulates in the plasma bound to von Willebrand factor. Patients with Hemophilia A exhibit reduced levels of factor VIII, which results in a reduction in blood clotting. Patients with a level of factor VIII less than 1% of normal have severe bleeding episodes throughout life. A level of about 5% of normal results in few, if any, spontaneous bleeding episodes, but severe bleeding can occur in these patients, for example, following surgery, if not properly managed. Patients with factor VIII levels of about 10 to 30% of normal have very mild hemophilia, but may still experience excessive bleeding, for example, following surgery.

Treatment of patients with hemophilia A generally involves administering factor VIII. The factor VIII may be obtained from human donors, or from animals, for example, porcine factor VIII. Recombinantly produced factor VIII may also be used. Severe hemophiliacs require frequent infusions of factor VIII to restore the blood's normal clotting ability. However, supplies of human factor VIII are often inadequate, and the time and expense involved in its isolation and purification from blood are considerable, especially in light of the risk of transmitting viruses such as AIDS and hepatitis.

About 15% of hemophilia A patients develop antibodies to factor VIII. These antibodies inhibit the anticoagulant activity of therapeutically administered factor VIII. Immune tolerance may be achieved through continuous exposure to factor VIII. This requires large and continuous infusions of factor VIII, which are costly, and, in the case of human-derived factor VIII, pose the risk of viral infection. Providing a means for extending the bioavailability of factor VIII would reduce the amount of factor VIII needed to treat hemophilia A patients.

In the opposite situation, if clotting factors are not degraded or inhibited once clotting begins, the blood clot can quickly spread within vessels and capillaries blocking blood flow to vital organs. Some of the leading causes of death in this country are the result of clotting diseases like stroke and myocardial infarction. Regulation of blood clotting will greatly influence therapeutic control over clotting and clotting diseases.

The steps involved in forming a clot include a series of zymogen activations (Roberts and Lozier, 1992). Zymogens are precursors of enzymes that are activated once they are proteolytically cleaved. The cleavage of the zymogen alters the protein structure exposing an active site and allowing enzymatic activity to occur. The coagulation process is interesting because many of the zymogens, when cleaved, become active serine proteases which have a specificity to cleave the next zymogen in the reaction. The activation of successive serine proteases provides a rapid response to a relatively small signal. Several steps in the process can be regulated to activate or inhibit clot formation.

Within the coagulation cascade, many of the serine proteases can also cleave inhibitors of the clotting process. The inhibitors are members of the family of proteins known as serpins ($_{ser}$ine $_{p}$rotease $_{in}$hibitor$_{s}$) (Potempa et al., 1994). Often, when a serpin is cleaved by a serine protease, the two proteins remain covalently bound, which inhibits the protease by preventing it from reacting with any other molecules (Mammen, 1998). One of the best examples of this is the interaction between the serine protease thrombin and the serpin antithrombin (AT).

Thrombin is the final protease generated in the clotting cascade, and is activated by the cleavage of prothrombin by Factor Xa (FIG. 1A). Thrombin can then cleave fibrinogen into fibrin monomers. Polymerization of fibrin monomers forms the fibrin part of the clot. Though activating fibrin is the main function of thrombin, it also has other functions. Thrombin can activate a positive feedback pathway by proteolytically activating Factors V and VIII that assist in the activation of prothrombin into thrombin. Thrombin also proteolytically cleaves proteins that can serve as inhibitors of its action.

Antithrombin is the most important anticoagulant in the blood (FIG. 1B). It has a high specificity for thrombin, but also weakly inhibits several other serine proteases. Antithrombin inhibits thrombin by inserting its reactive site loop into the active site of thrombin. The interaction forms a stable complex between the two molecules (Mammen, 1998).

The protease activity of thrombin cleaves the reactive site loop of antithrombin between an arginine and serine which are labeled P1 and P1' for the site of thrombin cleavage. The cleavage results in a covalent bond between antithrombin and thrombin and prevents thrombin from carrying out any further proteolytic reactions (Olson et al., 1995).

The binding between AT and thrombin occurs very slowly ($k_2=9\times10^3\ M^{-1}s^{-1}$) (Olson and Shore, 1982). In its native form, the reactive site loop of AT is not easily accessible to thrombin (Jin et al., 1997). Heparin, a polysaccharide with a strong negative charge, helps to speed this reaction (Olson and Shore, 1982). A specific pentasaccharide in heparin binds to the positively charged D-helix of AT (Jin et al., 1997; Olson et al., 1992). This causes AT to go through a structural change allowing the reactive site loop on AT to be more accessible to thrombin (Ersdal-Badju et al., 1997; Huntington and Gettins, 1998; Meagher et al., 1996). Heparin also binds to thrombin and acts as a bridge to draw the two molecules together (Danielsson et al., 1986). When heparin is bound to AT, the rate of reaction with thrombin is increased significantly (500- to 1000-fold) (Olson and Shore, 1982).

Although thrombin usually functions as a procoagulant, it can also activate the protein C pathway, an anticoagulant pathway. Thrombin has the ability to bind to an endothelial cell receptor called thrombomodulin (TM). When thrombin is bound to TM, it goes through a conformational change that results in a change in substrate specificity for protein C instead of fibrinogen (FIG. 1A) (Ye et al., 1991). Protein C interacts with thrombin through $Ca^{2+}$ bridges (Rezaie and Esmon, 1992). The protein C is cleaved by the thrombin bound to TM, generating activated protein C (APC). APC proteolytically degrades two cofactors of clotting, Factor Va and Factor VIIIa, preventing the activation of prothrombin to thrombin. Once activated, APC activity is accelerated when it is complexed with the cofactors protein S and Factor V. In other words, thrombin bound by TM becomes an anticoagulant by activating APC and forming a negative feedback pathway for thrombin activation.

Another member of the serpin family is protein C inhibitor (PCI). It has been found to serve several vital roles in the regulation of coagulation (FIG. 1B). Protein C inhibitor is a unique serpin because it has the ability to work as a procoagulant and an anticoagulant. Protein C inhibitor inhibits APC both directly and indirectly (Neese et al., 1994). It directly blocks APC activity by binding to its active site, similar to inhibition of thrombin by AT. When APC is inhibited by PCI, APC cannot degrade the clotting factors that activate prothrombin, Factors Va and VIIIa. Protein C inhibitor also has an increased ability to inhibit thrombin bound to TM (Elisen et al., 1998; Rezaie et al., 1995). When TM-bound thrombin is inhibited by PCI, protein C cannot access it, which prevents activation of protein C. The inhibition of APC and TM-bound thrombin by PCI blocks both the activation and activity of protein C allowing the production of thrombin to continue. By inhibiting the negative feedback pathway, PCI acts as a procoagulant.

Protein C inhibitor also can directly inhibit thrombin. The reactive site loop of PCI is compatible with the active site of thrombin and when cleaved it forms a covalent bond similar to that between AT and thrombin (Cooper and Church, 1995). Based on inactivation reactions in the absence of heparin, PCI inhibits thrombin faster than AT suggesting that its reactive site loop fits better in the active site of thrombin (Rezaie, 1997). While heparin increases the activity of AT with thrombin by 300-fold, it only increases the activity of PCI with thrombin by 20- to 30-fold (Shirk et al., 1994). This difference suggests that heparin binding does not cause as many structural changes in PCI as in AT.

As mentioned previously, thrombin binding to TM does not prevent its inactivation by the serpins. Inhibition by AT increases when the thrombin is bound to TM, but only if a heparin-like polysaccharide, chondroitin sulfate, is also attached to the TM (Bourin et al., 1986; Bourin et al., 1988). It is believed that the chondroitin sulfate binds to the heparin binding site of AT and the heparin binding exosite 2 of thrombin and functions similarly to heparin (Weisel et al., 1996). However, the increase in activity is fairly small (4-fold) compared to free thrombin in the presence of heparin (300-fold) (Preissner et al., 1987). While the activity of PCI with free thrombin is fairly low ($k_2$=1.7×$10^4$ $M^{-1}s^{-1}$), when thrombin is bound by TM, PCI becomes a very strong inhibitor of thrombin activity ($k_2$=2.4×$10^6$ $M^{-1}s^{-1}$) (Rezaie et al., 1995). Though AT needs chondroitin sulfate to have a pronounced effect on TM-bound thrombin, PCI is not as sensitive to chondroitin sulfate (2-fold greater than without chondroitin sulfate) (Rezaie et al., 1995). Because heparin does not have a strong affect on PCI, it could be assumed that chondroitin sulfate would not affect PCI as strongly either.

The most important domains of TM are a series of six epidermal growth factor (EGF)-like motifs. It has been determined that domains 5 and 6 are responsible for TM binding thrombin, but thrombin cannot activate protein C when it is bound by these two regions alone (Ye et al., 1991). When domain 4 is included with 5 and 6, thrombin changes its conformation giving it similar enzymatic rates to thrombin complexed with full membrane-bound TM (Hayashi et al., 1990).

Although the general structures and functions of PCI and AT are similar, different amino acid sequences in the heparin binding domains and reactive site loops are believed to be responsible for the observed differences in function (Cooper and Church, 1995). Molecular modeling and mutagenesis studies have shown that heparin binding sites differ between AT and PCI (Cooper et al., 1995; Neese et al., 1998). In AT, heparin binds to the D-helix region (Jin et al., 1997), but in PCI, it has been found to bind to the H-helix (Neese et al., 1998). The H-helix on both proteins is in a position that would require heparin to bend in order to bind both thrombin and the serpin. This may be a reason why heparin and chondroitin sulfate have a reduced affect on acceleration of thrombin inhibition by PCI compared with AT.

There are important differences between the sequence of the H-helix of AT and PCI, as shown below in Table 1. The difference in the sequence of the H-helix could affect how each protein interacts with heparin and inhibits thrombin. Heparin binds to proteins using positively charged residues on $\alpha$-helices. The H-helix of AT contains amino acid residues with negative charges, but the H-helix of PCI is mainly composed of positive and neutral residues (Shirk et al., 1994). First, two positive residues on the H-helix of PCI, $Arg^{269}$ and $Lys^{270}$, are known to contribute to heparin interactions with PCI (Shirk et al., 1994). The corresponding positions of AT contain a neutral $Gln^{305}$ and a negative $Glu^{306}$ which would repel heparin (Shirk et al., 1994). Second, the carboxy terminus of the H-helix is also considerably different between the two serpins. Protein C inhibitor contains positive and neutral residues while AT has mainly negative residues (Shirk et al., 1994). It is unknown whether this region of the helix is important for PCI to bind heparin. The negative charges in this region in AT could contribute steric effects and prevent heparin from binding to the H-helix on AT. Third, another difference near the H-helix is the presence of an arginine at position 278 in PCI that may form a salt bridge with $Glu^{39}$ of thrombin in complexes with PCI, but AT has a methionine in the corresponding position at residue 314 (Cooper and Church, 1995).

TABLE 1

| | | | | | | | | | | | |
|---|---|---|---|---|---|---|---|---|---|---|---|
| | | | | | | | | | | | [SEQ ID NO: 7] |
| PCI | $^{268}$L | R | K | W | L | K | M | F | K | K | $R^{278}$ |
| | | | | | | | | | | | [SEQ ID NO: 8] |
| AT | $^{304}$L | Q | E | W | L | D | E | L | E | E | $M^{314}$ |

Another region in which differences in sequence could greatly affect thrombin inhibition is in the reactive site loop. Differences in inhibition rates among serpins suggest that reactive site loops may possess residues that fit better with different conformations of thrombin. For example, PCI inhibits thrombin bound to TM better than free thrombin suggesting that a conformational change in the active site of thrombin allows it to accommodate the residues in the reactive site loop of PCI (Le Bonniec and Esmon, 1991; Rezaie, 1997; Rezaie et al., 1995).

Comparison of the sequences of the reactive site loops of AT and PCI (shown below in Table 2) demonstrates that between P3 and P3', only the P1 and P1' residues are conserved. The P1 arginine and P1' serine are important to proper serpin function because thrombin cleaves the reactive site loop between these two residues (Stephens et al., 1988). While the surrounding residues are not directly involved in the cleavage, they are inserted into the active site of thrombin and contribute to the association between the reactive site loop and the active site loop of thrombin. Because thrombin can be found in several different conformations, mutations in the reactive site loop of the serpins would be useful to modulate the insertion of the reactive site loop into different configurations of the active site of thrombin, thereby modulating thrombin activity and consequently modulating coagulation. This would be especially useful in the treatment of diseases involving deficiencies of coagulation factors.

TABLE 2

| | P4 | P3 | P2 | P1 | P1' | P2' | P3' | P4' |
|---|---|---|---|---|---|---|---|---|
| | | | | | | | | [SEQ ID NO: 13] |
| PCI | Phe | Thr | Phe | Arg | Ser | Ala | Arg | Leu |
| | | | | | | | | [SEQ ID NO: 14] |
| AT | Ile | Ala | Gly | Arg | Ser | Leu | Asn | Pro |

In summary, agents for modulation of the clotting cascade, for example that modulate thrombin activity, are needed for the treatment of clotting diseases.

SUMMARY OF THE INVENTION

The invention provides mutants of antithrombin (AT) modified in the H-helix and reactive site loop sequence, having modulated activity in the inhibition of thrombin. In particular, AT modified to have a greater positive charge in the H-helix (AT-pos), has enhanced inhibitory activity against thrombin bound to thrombomodulin (T-TM), at a level which resembles the procoagulant activity of Protein C Inhibitor (PCI). The AT-pos mutants retain AT ability to inhibit free thrombin, but, due to its enhanced activity against T-TM, the AT-pos mutants effectively shut down the T-TM activation of Protein C, inhibiting Activated Protein C degradation of Coagulation Factors V, VIII, and X.

The invention provides nucleic acids encoding AT-pos mutants, amino acid sequences of AT-pos mutants, pharmaceutical compositions containing AT-pos mutants, and methods of treating patients deficient in one or more coagulation Factors, for example, hemophiliacs, and methods for extending the bioavailability of Factor VIII in a patient. In particular, the invention provides AT-pos mutants and methods for their use in extending the bioavailability of Factor VIII.

BRIEF DESCRIPTION OF THE DRAWINGS

FIGS. 1A and 1B are schematic diagrams showing the final stages of coagulation and the Protein C pathway, and inhibition by PCI and AT.

FIG. 2 is a schematic drawing showing the subcloning strategy used to generate recombinant antithrombin mutants.

FIG. 3 is a graph showing heparin accelerated thrombin inhibition by AT.

DETAILED DESCRIPTION OF THE INVENTION

The phrase "effective amount", as used herein, is an amount of an agent that is sufficient to cause a desired result, especially when the agent is administered to an animal or human.

The term "enhanced", as used herein, means a greater activity or amount as compared with an appropriate control.

The term "bioavailability", as used herein, refers to the presence of factor VIII in circulation.

A "pharmaceutical composition", as used herein, includes solvents, carriers, diluents, and the like, which are utilized as additives or vehicles in compounds containing modified antithrombin that are to be administered to animal or human patients.

The term "treating" or "treatment", as used herein, means the administration of the modified antithrombin in an effective amount to a patient for purposes which may include prophylaxis, amelioration, prevention, or cure of a medical disorder or disease.

Antithrombin

Antithrombin (AT) is a potent anticoagulant serpin, as discussed above in the Background of the Invention. The nucleic acid sequence encoding AT is known (Gen Bank No: ref|NM_000488.1 gi:4502260 Homo sapiens antithrombin III (AT3) mRNA) [SEQ ID NO: 6]. AT has activity against both free thrombin (T) and thrombin bound to thrombomodulin (TM), however, its activity against the bound form, T-TM is dependent upon the presence of chondroitin sulfate, and is less than other serpins, for example, protein C inhibitor (PCI).

Figure 1A:
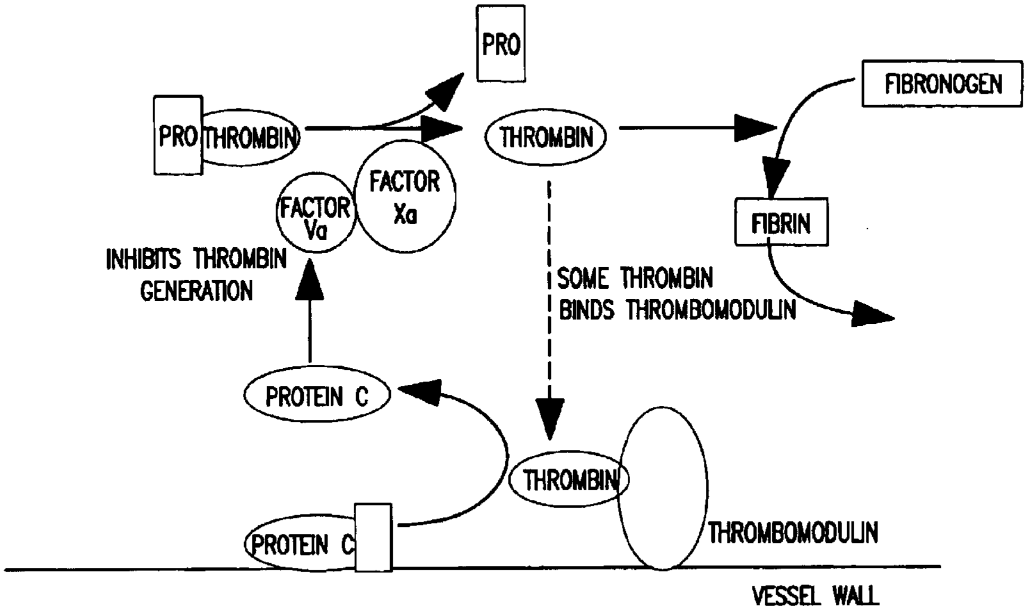
Figure 1B:
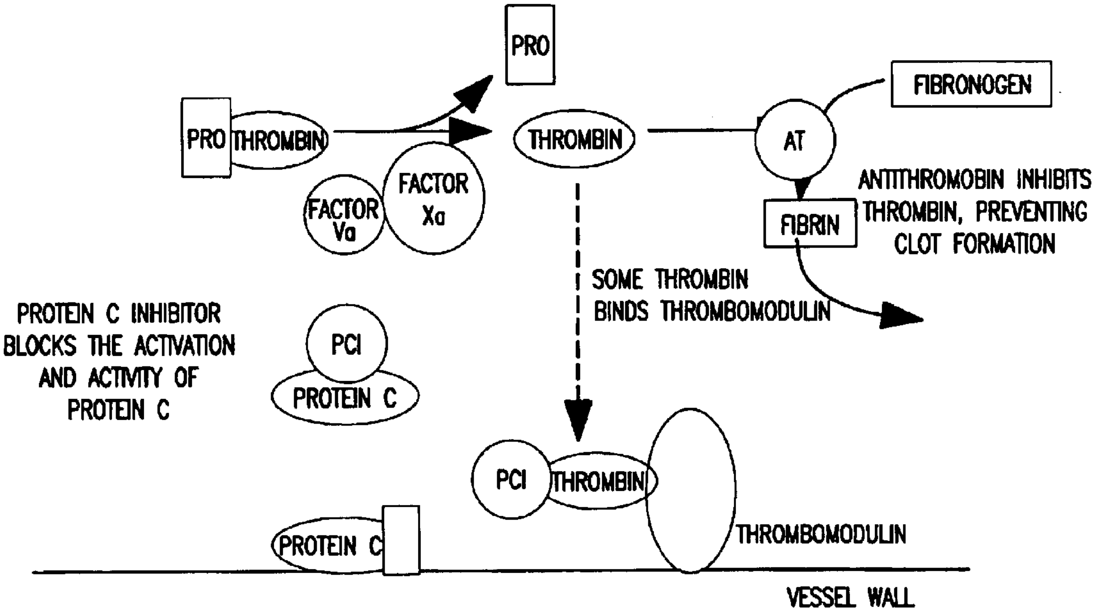

AT-pos mutants, having enhanced positive charge in the H-helix have antithrombin activity that is altered. The AT-pos mutants have enhanced inhibitory activity against T-TM, as demonstrated in the Examples below. As shown in FIGS. 1A and 1B, inhibition of T-TM prevents the T-TM induced activation of protein C, shutting down a feed-back loop for thrombin production and preventing activated protein C from degrading specific coagulation factors, including Factors V and X, and also Factor VIII.

The H-helix of AT has been schematically shown and described (Cooper et al., 1995; Neese et al., 1998). Specific amino acid residues within the H-helix of AT are compared with those of the H-helix of PCI in Table 2 above, and with an AT-pos mutant, and other AT mutants in the Examples below. In a preferred embodiment of the invention, this region of the AT-H-helix, spanning amino acid residues 304–314 of wild type antithrombin (WT-AT), is modified to increase its overall positive charge. The desired modification may be substitution of a negatively charged amino acid with a neutral or positively charged amino acid; or may be the substitution of a neutral amino acid with a positively charged amino acid. Insertion of positively amino acids and/or deletion of negatively charged amino acids is also contemplated, provided the three dimensional structure of the molecule required for thrombin binding is maintained.

In a most preferred embodiment, one or more of the amino acids is substituted with a positively charged amino acid (e.g., lysine (lys, K) or arginine (arg, R)), for example, replacing one or more of amino acids 309, 310, 312, and 313 with a positively charged amino acid, such as lysine (K) or arginine (R), preferably K.

The AT-pos mutants of the invention can be produced by methods known in the art, and as described in the Examples below. FIG. 2 shows one subcloning strategy for producing the desired mutants.

Modulation of Thrombin

The AT-pos mutants of the invention modulate the activity of thrombin in a manner that is functionally distinct from native AT. While retaining inhibitory activity against free thrombin, the AT-pos mutants have enhanced inhibitory activity against the bound form, T-TM. Inhibition of the bound T-TM blocks a negative feedback loop, the inhibition resulting in enhanced production of thrombin.

AT-pos Prevents Degradation of Coagulation Factors

The enhanced ability of the AT-pos mutants to inhibit T-TM, and thereby to inhibit the activated protein C degradation of coagulation factors V, X, and VIII extends the bioavailability of these coagulation factors. This is particularly useful in treating hemophilia patients deficient in one or more coagulation factors. The most prevalent defect is a lack of Factor VIII. A common therapy for these patients is the replacement of the protein factor, for example Factor VIII. The AT-pos mutants of the invention are useful in preventing the degradation of these coagulation factors, and thus extending the bioavailability of the Factors in a therapeutic setting.

The bioavailability of factor VIII in the presence or absence of the AT-pos mutants of the invention can be evaluated in various animal models. After co-administration of factor VIII with AT-pos to animals, factor VIII can be analyzed in blood samples, for example by immunoassay, affinity chromatography, radiolabel clearance assay, or other known methods. Functional activity can also be analyzed, e.g., clotting times.

Several animal models for human hemophilia are available for analysis of AT-pos effects in extending the activity of factor VIII. These include mice genetically deficient in factor VIII (Bi et al., 1995; Bi et al., 1996; Wu et al., 2001) and rabbits and mice with antibody-induced hemophilia (Turecek et al., 1997).

Pharmaceutical Compositions

Pharmaceutical compositions comprising modified antithrombin and suitable stabilization compounds, delivery vehicles and/or carriers are prepared by known techniques. In one embodiment, the stabilization compounds and carriers used for intravenous infusion are physiological saline or phosphate buffered saline. In an alternative embodiment, the stabilization compounds and carriers include, but are not limited to, other human or animal proteins such as albumin. In a further embodiment, the modified antithrombin is added to a standard factor VIII composition used for treating hemophiliacs.

Treatment

Modified AT is used to treat uncontrolled bleeding episodes due to factor VIII deficiency in hemophiliacs. The modified AT is preferably administered intravenously. The modified AT is also used to prevent or reduce the occurrence of uncontrolled bleeding episodes in factor VIII deficient hemophiliacs when administered with factor VIII. The modified AT extends the bioavailability of native factor VIII or of therapeutically administered factor VIII by inhibiting the activity of thrombin bound to thrombomodulin, by inhibiting the activation of Protein C, and by inhibiting Activated Protein C degradation of factor VIII.

In treating hemophilia A patients with factor VIII products, the desired outcome is to raise the level of factor VIII to between about 0.3 U (30%) and 1.0 U (100%), depending on the presence and severity of an uncontrolled bleeding episode. The dose of factor VIII is generally calculated by multiplying the patient's weight by a standard factor and by the desired plasma level in units. For example, if the patient's weight is in kilograms, a standard factor is 44, and if the weight is in pounds, a standard factor is 20. Administration of AT-pos extends the length of time these levels of factor VIII are present in the bloodstream of the patient, and reduces the frequency and/or dosage of factor VIII infusions needed by the patient.

Administration of an effective amount of AT-pos will maintain a desired level of factor VIII in the patient's bloodstream for an extended period as compared to a non-AT-pos control. The dose of AT-pos to be administered can be determined by the one-stage factor VIII coagulation assay. In vivo recovery may be determined by measuring factor VIII in the patient's plasma after infusion.

In general a suitable dose of AT-pos may be from about 0.1 mg/kg to about 1000 mg/kg, preferably from about 1 mg/kg to about 100 mg/kg, and more preferably about 10 mg/kg to about 50 mg/kg. In general, a suitable plasma concentration of AT-pos may be about 10 nM to about 1000 nM or approximately 0.1 $\mu$g/ml to approximately 100 $\mu$g/ml.

AT-pos will generally be co-administered along with Factor VIII, for example at a molar ratio of approximately 1:1, and for example, by injection or infusion. When formulated for oral delivery, the administered dose of Factor VIII and of AT-pos will generally be greater than the injected dose.

It is to be understood that the concentration ranges set forth herein are exemplary only and are not intended to limit the scope or practice of the claimed composition, and that the dosage and frequency of both factor VIII and AT-pos administered to a particular patient are to be adjusted over time according to the patient's need and based on the professional judgment of the person administering or supervising the administration of the compositions.

EXAMPLES

The following Examples serve to illustrate specific embodiments of the invention and are not intended as limiting.

Example 1

Production of Mutant-AT

Mutagenesis of the H-helix. The H-helix is a positively charged heparin binding domain on PCI and may contribute to its decreased inhibition of thrombin in the presence of heparin and the increased inhibition of thrombin bound by TM. In contrast, the H-helix of AT is negatively charged, and would repel heparin from binding to that region. Mutations were introduced into the H-helix of AT to alter its modulation of thrombin.

The H-helix of AT was divided into three regions and mutated to resemble the H-helix of PCI. Mutant AT-RK was designed to replace $Gln^{305}$ (Q) and $Glu^{306}$ (E) with the arginine (R) and lysine (K) found in the corresponding positions of PCI, as these residues have been found to contribute to heparin binding. To address the importance of the carboxy terminus of the H-helix, the negatively charged $Asp^{309}$ (D) and $Glu^{310, 312, 313}$ (E) of AT were replaced with a neutral asparagine (Asn, N) in position 309 and neutral glutamines (Gln, Q) in positions 310, 312 and 313 (AT-neut) and with lysine (Lys, K) in all four positions (AT-pos). To examine the possibility of a salt bridge forming between $Glu^{39}$ in thrombin and the residue at position 314 in AT, this residue was changed from methionine to arginine (Arg, R).

Table 3 (below) shows the amino acid sequences of the H-helices of protein C inhibitor, antithrombin, and antithrombin H-helix mutants.

TABLE 3

| | | | | | | | | | | | | |
|---|---|---|---|---|---|---|---|---|---|---|---|---|
| PCI | $^{268}$L | $R^2$ | $K^2$ | W | L | $K^2$ | M | F | $K^2$ | $K^2$ | $R^{278}$ | [SEQ ID NO: 7] |
| AT | $^{304}$L | Q | $E^1$ | W | L | D | $E^1$ | L | $E^1$ | $E^1$ | $M^{314}$ | [SEQ ID NO: 8] |
| AT-RK | $^{304}$L | $R^2$ | $K^2$ | W | L | $D^1$ | $E^1$ | L | $E^1$ | $E^1$ | $M^{314}$ | [SEQ ID NO: 9] |
| AT-pos | $^{304}$L | Q | $E^1$ | W | L | $K^2$ | $K^2$ | L | $K^2$ | $K^2$ | $M^{314}$ | [SEQ ID NO: 10] |
| AT-neut | $^{304}$L | Q | $E^1$ | W | L | N | Q | L | Q | Q | $M^{314}$ | [SEQ ID NO: 11] |
| AT-314R | $^{304}$L | Q | $E^1$ | W | L | $D^1$ | $E^1$ | L | $E^1$ | $E^1$ | $R^{314}$ | [SEQ ID NO: 12] |

($^1$negative residues; $^2$positive residues)

Mutagenesis of the reactive site loop sequence. Mutating the reactive site loop of AT to mimic the reactive site loop of PCI demonstrated the role of the reactive site loop in the inhibition of different conformations of thrombin. The AT reactive site loop was replaced with the corresponding sequence of the PCI reactive site loop in AT-rsl. Table 4 shows amino acid sequences of the reactive site loops (P4–P4') of PCI, AT, and AT reactive site mutants (substituted residues are underlined).

Protein C inhibitor mutants with an arginine at P3 have shown an increase in thrombin inhibition. Therefore mutant AT-P3R contains the PCI reactive site loop with an arginine at the P3 position (Cooper and Church, 1995). These are all novel mutations, which have not been previously examined in AT.

Plasmid Construction. Wild-type AT cDNA (Prochownik et al., 1983) was excised from the plasmid pKT218 (ATCC, Manassas, Va.) with $_{Pst}$ I (FIG. 2). A polylinker for $_{Bam}$H I was added to the 3' end of the cDNA by polymerase chain reaction amplification. The PCR fragment was ligated into pGEM3Zf(+) at the $_{Pst}$ I and $_{Bam}$H I restriction sites.

Site-directed Mutagenesis. Specific mutations were generated with the QuickChange Site-Directed Mutagenesis Kit (Stratagene, Cambridge, UK) that uses a PCR thermal cycler and overlapping mutagenesis primers containing the desired mutations to amplify the plasmid and cDNA and insert the mutations as part of the primer. Mutagenesis primers were obtained from Integrated DNA Technologies (Coralville, Iowa). The PCR product was digested with $_{Dpn}$ I to remove all methylated template DNA leaving only amplified plasmids with the cDNA containing the desired mutations. Plasmids containing mutated DNA were transformed into *E. coli* by a heat shock transformation. Ampicillin was used to select for transformants.

TABLE 4

| | P4 | P3 | P2 | P1 | P1' | P2' | P3' | P4' | |
|---|---|---|---|---|---|---|---|---|---|
| PCI | Phe | Thr | Phe | Arg | Ser | Ala | Arg | Leu | [SEQ ID NO: 13] |
| AT | Ile | Ala | Gly | Arg | Ser | Leu | Asn | Pro | [SEQ ID NO: 14] |
| AT-rs1 | Ile | <u>Thr</u> | <u>Phe</u> | Arg | Ser | <u>Ala</u> | <u>Arg</u> | Pro | [SEQ ID NO: 15] |
| AT-P3R | Ile | <u>Arg</u> | <u>Phe</u> | Arg | Ser | <u>Ala</u> | <u>Arg</u> | Pro | [SEQ ID NO: 16] |

The AT mutants were made by site-directed mutagenesis of the AT cDNA. Mutant proteins were expressed in the Baculovirus expression system (Gillespie et al., 1991) and purified with heparin affinity columns. Protein purity and concentration was determined using immunoblot and ELISA. The inhibition of thrombin was determined by discontinuous enzymatic assays with the recombinant proteins in the presence and absence of heparin and thrombomodulin. The rate of inhibition by the recombinant proteins of factor Xa, APC, and trypsin were also determined.

Primers used for Mutagenesis of AT

```
H-helix mutant QE to RK       33-mer                    [SEQ ID NO:1]
cca gag gtg ctg cgg aag tgg ctg gat gaa ttg

H-helix mutant Poly-K         42-mer                    [SEQ ID NO:2]
gag tgg ctg aaa aaa ttg aag aag atg atg ctg gtg gtt cac

H-helix mutant Poly-A         42-mer                    [SEQ ID NO:3]
gag tgg ctg gct gca ttg gcg gcg atg atg ctg gtg gtt cac

H-helix mutant M314R          30-mer                    [SEQ ID NO:4]
gaa ttg gag gag agg atg ctg gtg gtt cac

Reactive site loop mutant     45-mer                    [SEQ ID NO:5]
gct gtt gtg att asa ttc cgt tcg gca aga ccc aac agg gtg act
```

Sequencing. Plasmids were isolated using a QIAprep Miniprep Kit (QIAgen, Valencia, Calif.). A Thermo Sequenase radiolabeled terminator cycle sequencing kit (Amersham Pharmacia, Arlington Heights, Ill.) was used to sequence the AT cDNA to ensure that no errant mutations were inserted during the mutagenesis reaction. Sequencing products were separated on glycerol tolerant 6% polyacrylamide gels using TTE buffer (89 $m_M$ Tris, 30 $m_M$ Taurine, 0.5 $m_M$ EDTA) and exposed to film.

Subcloning into Transfer Vector. Wild-type AT was excised from pGEM3Zf(+) containing the cDNA with $_{Pst}$ I and $_{Bam}$H I and subcloned into the baculovirus transfer vector pVL1392. The last 500 bases of each mutated AT cDNA, containing the site-directed changes, were excised from pGEM3Zf(+) with $_{Nco}$ I and $_{Bam}$H I. The wild-type AT cDNA in pVL1392 was also digested with $_{Nco}$ I and $_{Bam}$H I, and the mutated $_{Nco}$ I and $_{Bam}$ H I fragments were ligated into the place of the wild-type fragment in pVL1392. The 500-base pair fragment was sequenced to ensure that DNA containing the correct mutations had been subcloned.

Expression and Purification of AT. Transfer vectors (pVL1392) containing either the wild-type or mutant AT cDNAs were cotransfected along with Baculogold *Autographa californica* polyhedrosis virus DNA into S∂9 (*Spodoptera frugiperda*) host insect cells in TMN-FH complete media using the Baculovirus Expression Vector System (PharMingen, San Diego, Calif.). Within the host cells, the cDNA can go through a homologous recombination with the viral DNA producing a viral stock that contains virus with the AT cDNA. Recombinant viral stocks were collected four days post-infection and the viral titer was amplified by infection of new S∂9 cells. Amplified viral stocks were used to infect the High-Five cell line (*Tricoplusia ni*) in ExCell serum-free medium (JRH Biosciences, Lenexa, Kans.) with 1 $m_M$ L-glutamine and 5 μg/ml gentamicin. Three days post-infection, media was collected and centrifuged to remove cell debris. Media containing recombinant AT was applied to heparin affinity columns equilibrated with either TCE (0.05$_M$ Tris, 0.02$_M$ citrate, 5.0 $m_M$ EDTA, 0.02% azide, 0.1$_M$ NaCl, pH 7.4) or HNPN (20 $m_M$ HEPES, 150 $m_M$ NaCl, 0.1% PEG, 0.05% azide, pH 7.4) buffer. After applying the sample to the column, it was washed with buffer and the protein was eluted with TCE or HNPN buffer containing 2$_M$ NaCl. The eluted sample was dialyzed in either TCE or HNPN buffer to remove excess salt.

Immunoblot and Enzyme-Linked Immunosorbent Assay. Proteins from infected cells and media were subjected to sodium dodecyl sulfate-polyacrylamide gel electrophoresis (SDS-PAGE) and then transferred to NitroBind nitrocellulose transfer membrane (Micron Separations Inc., Westboro, Mass.). The membrane was blocked for 20 minutes with TBST (10 $m_M$ Tris, 150 $m_M$ NaCl, 0.05% Tween 20, pH 7.5) containing 1% milk. Polyclonal rabbit anti-AT antiserum was used as the primary antibody (1:2000 dilution with TBST-milk) and goat anti-rabbit IgG conjugated with alkaline phosphatase was used for the secondary antibody (1:20,000 dilution with TBST-milk). Antibodies were incubated for 30 minutes at room temperature. The membrane was washed with TBST between each application of the antibodies and the substrate. Nitroblue tetrazolium/5-bromo-4-chloro-3-indolyl phosphate were used as substrates to visualize the bands bound by the antibodies.

Following initial purification of each recombinant protein, all column flow-throughs and eluted fractions were tested by ELISA to ensure that mutations did not prevent protein from binding to heparin. Subsequent ELISAs were only performed on the elution fraction. Purified human AT was used as a standard at concentrations from 0.125 to 8 $n_M$. Samples were diluted between 100- to 500-fold in TBS buffer (10 $m_M$ Tris, 150 $m_M$ NaCl, pH 7.5) and bound to a 96-well microtiter plate and incubated for at least one hour at 37° C. or overnight at 4° C. The plate was blocked with TBST-milk, followed by antibody incubations and washes as described for the immunoblot at 37° C. $_p^-$ Nitrophenyl phosphate, diluted in AP buffer (0.1$_M$ Tris, 0.1$_M$ NaCl, 5 $m_M$ $MgCl_2$, pH 9.5), was used as a substrate and colorimetric quantification was accomplished using a SpectraMax Plus plate reader (Molecular Devices, Sunnyvale, Calif.).

Serine Protease Inhibition Assays. The rates of inhibition of the serine proteases thrombin, factor Xa and APC in the presence and absence of heparin were measured using discontinuous assays under pseudo-first order rate conditions as described previously (Phillips et al., 1994; Rezaie et al., 1995). Protein was diluted in TBS buffer containing 0.1 mg/ml BSA, 0.1% PEG 8000, and 0.01% azide to a final reaction volume of 50 μl. The serine protease and a ten-fold molar excess of various forms of AT were incubated together. After a period of time (15 seconds to 30 minutes based on inhibition rate), 50 μl of calorimetric substrate was added. Substrates used were Spectrozyme TH (SpTH) for thrombin and trypsin, PCA (SpPCA) for APC, and FXa (SpFXa) for Factor Xa (American Diagnostica, Greenwich, Conn.). Absorbances were determined using a SpectraMax Plus plate reader (Molecular Devices, Sunnyvale, Calif.). Absorbance is directly related to residual protease activity. In assays containing heparin, 1 mg/ml Polybrene was added to the substrate to block further heparin binding during substrate development. For heparin template curve data, varying concentrations (0–1000 μg/ml) of unfractionated heparin were added and proteins were diluted in HNPN buffer. For remaining heparin assays, the resulting optimal heparin concentration (5 μg/ml) was used. All enzymes used were purified and activated from human plasma (provided by Dr. Frank Church and Dr. Alireza Rezaie). TM was either purified rabbit TM (RTM) or recombinant 4–6 TM (provided by Dr. Alireza Rezaie). Second-order rate constants of thrombin inhibition were determined using the following equation:

$$k_2=(-\ln A/A_0)/t[I]$$

where A is the absorbance of the inhibited sample, $A_0$ is the absorbance of uninhibited sample, t is time of reaction in seconds and [I] is the concentration of AT in moles/liter (Phillips et al., 1994; Rezaie et al., 1995). All assays were performed in triplicate in two to five separate experiments.

Expression of AT. The wild-type recombinant AT (rAT) and all of the mutant proteins were successfully expressed in Hi5 cells using the Baculovirus expression system. Immunoblots of the media from the cotransfections demonstrated that none of the recombinant proteins had been degraded (data not shown). The molecular weight of the rAT was slightly lower than plasma AT due to differences in glycosylation (Gillespie et al., 1991). Following heparin affinity purification, ELISAs of the column flow-through and elution fractions identified that the mutant AT proteins bound to the column and eluted from the column with the 2 M NaCl elution buffer (data not shown).

Example 2

Role of the H-helix of AT in the Inhibition of Thrombin

Inhibition in the presence of heparin. Thrombin inhibition is accelerated (300- to 1000-fold) in the presence of heparin (Olson et al., 1992). To examine whether mutation of the H-helix had altered heparin acceleration of thrombin inhibition, inhibition assays of thrombin were performed in the presence and absence of heparin, using the assay method described for Example 1. Changes in heparin binding domains may alter the concentration of heparin required for the fastest rate of thrombin inhibition.

Results of the assay showed that plasma AT, rAT, and the H-helix mutant proteins all had an optimal heparin concentration of 5 μg/ml (FIG. 3). Heparin acceleration of the reaction between AT-pos and thrombin was lowest at all heparin concentrations, compared with the other H-helix mutants and the rAT (FIG. 3). Subsequent assays with heparin were done at the optimal heparin binding concentration of 5 μg/ml heparin.

Wild-type rAT and plasma AT showed a 217- and 312-fold acceleration of thrombin inhibition, respectively, in the presence of heparin (Table 5). Due to decreased glycosylation, lower activity is expected from recombinant proteins compared with proteins purified from plasma (Gillespie et al., 1991). With the exception of AT-pos, the H-helix mutant proteins showed similar degrees of heparin acceleration of thrombin inhibition compared to the recombinant wild-type version (200- to 300-fold).

AT-pos inhibition of thrombin was accelerated 34-fold in the presence of heparin. This value is close to the 20-fold heparin acceleration of thrombin inhibition by PCI (Rezaie et al., 1995).

TABLE 5

Second-order rate constants ($k_2$) of thrombin inhibition by antithrombin in the presence and absence of heparin

| | Heparin | | Ratio |
|---|---|---|---|
| AT | − | + | (+/−) |
| plasma AT | $8.9 \times 10^{3a}$ | $2.8 \times 10^6$ | 312 |
| rAT | $6.9 \times 10^3$ | $1.5 \times 10^6$ | 217 |
| H-helix | | | |
| AT-RK | $2.3 \times 10^3$ | $6.5 \times 10^5$ | 281 |
| AT-pos | $5.3 \times 10^3$ | $1.8 \times 10^5$ | 34 |
| AT-neut | $4.9 \times 10^3$ | $1.4 \times 10^6$ | 285 |
| AT-314R | $7.1 \times 10^3$ | $1.5 \times 10^6$ | 207 |
| Reactive site loop | | | |
| AT-P3R | $4.8 \times 10^3$ | $1.3 \times 10^6$ | 263 |
| AT-rs1 | $3.0 \times 10^3$ | $6.3 \times 10^5$ | 210 |

[a]All $k_2$ values are in units of $M^{-1}$ $sec^{-1}$

Inhibition in the presence of TM. Thrombin shows nearly normal levels of protein C activation when bound only by the 4–6 EGF repeats of TM (4–6 TM) (Phillips et al., 1994; Shirk et al., 1994). However, inhibition of 4–6 TM-bound thrombin by AT is minimal due to the absence of any cofactor (i.e., heparin or chondroitin sulfate). Protein C inhibitor inhibits both thrombin bound to full-length TM and 4–6 TM at approximately similar levels (Rezaie et al., 1995). To examine whether any of the H-helix mutants had gained the ability to inhibit thrombin bound to 4–6 TM, inhibition assays were performed. Inhibition of thrombin bound to 4–6 TM only changed slightly (0.5- to 1.7-fold) in the plasma derived AT, rAT, and most recombinant H-helix mutant proteins of AT (Table 6). The exception was AT-pos inhibition of thrombin, which increased by 3.7-fold in the presence of 4–6 TM when compared to inhibition in the absence of TM.

TABLE 6

Second-order rate constants ($k^2$) of thrombin inhibition by AT in the presence of 4–6 TM

| | 4–6 TM | | Ratio |
|---|---|---|---|
| AT | − | + | (+/−) |
| plasma AT | $9.5 \times 10^{3a}$ | $7.4 \times 10^3$ | 0.8 |
| rAT | $3.9 \times 10^3$ | $2.6 \times 10^3$ | 0.6 |
| H-helix | | | |
| AT-RK | $1.6 \times 10^3$ | $8.8 \times 10^2$ | 0.5 |
| AT-pos | $5.5 \times 10^3$ | $2.0 \times 10^4$ | 3.7 |
| AT-neut | $4.1 \times 10^3$ | $4.9 \times 10^3$ | 1.2 |
| AT-314R | $4.9 \times 10^3$ | $8.5 \times 10^3$ | 1.7 |
| Reactive site loop | | | |
| AT-P3R | $2.0 \times 10^3$ | $1.2 \times 10^3$ | 0.6 |
| AT-rs1 | $3.4 \times 10^3$ | $2.5 \times 10^3$ | 0.7 |

[a]All $k_2$ values are in units of $M^{-1}$ $sec^{-1}$

To investigate the role of TM further, AT-pos was assayed in the presence and absence of RTM which contains chondroitin sulfate as a cofactor. When thrombin was bound to RTM, plasma AT showed a 3.1-fold increase in inhibition and rAT increased inhibition of thrombin 28-fold (Table 7). AT-pos had a greater than 90-fold increase in thrombin inhibition when the thrombin was bound by RTM, which made it a very strong inhibitor of TM-bound thrombin when cofactor was present.

TABLE 7

Second-order rate constants ($k_2$) of thrombin inhibition by AT-pos in the presence of 4–6 TM and rabbit thrombomodulin (RTM)

| | TM | | | Ratio to no TM | |
|---|---|---|---|---|---|
| AT | No TM | 4–6 TM | RTM | 4–6 TM | RTM |
| plasma | $9.4 \times 10^{3a}$ | $9.4 \times 10^3$ | $2.9 \times 10^4$ | 1.0 | 3.1 |
| rAT | $4.8 \times 10^3$ | $7.1 \times 10^3$ | $1.3 \times 10^5$ | 1.5 | 28.0 |
| AT-pos | $6.4 \times 10^3$ | $1.9 \times 10^4$ | $5.8 \times 10^5$ | 3.0 | 90.7 |

[a]All $k_2$ values are in units of $M^{-1}$ $sec^{-1}$

Example 3

Role of the H-helix of AT in the Inhibition of Other Serine Proteases

Because AT can also inhibit many other serine proteases, assays were performed to determine if the mutations had altered residues involved in inhibition of other serine proteases. Because the mutant proteins were designed to resemble sections of the H-helix of PCI, a natural inhibitor of APC, inhibition assays were completed to examine whether the mutations would affect APC activity. Inhibition of APC was minimal in the plasma-derived AT, the recombinant AT and all of the H-helix mutant proteins (data not shown).

Factor Xa is a serpin that is similar in structure to thrombin. Antithrombin inhibits Factor Xa only 3-fold slower than it inhibits thrombin, but PCI inhibition of Factor Xa is 1000-fold slower than AT inhibition of Factor Xa (Cooper et al., 1995; Rezaie, 1998). The H-helix mutant proteins inhibited Factor Xa at similar rates to the wild-type rAT (Table 8).

Trypsin is a very general serine protease, and displays less substrate specificity than other proteases. Trypsin inhibition assays were performed to examine the overall activity of each mutant protein. The results show that while some are less active than the wild-type AT, all the H-helix mutant proteins are active to some degree and none of the mutant proteins showed differences from the wild-type (Table 8).

TABLE 8

Second order rate constants ($k_2$) of Factor Xa and trypsin inhibition by antithrombin

| AT | Factor Xa | Trypsin |
|---|---|---|
| plasma AT | $2.7 \times 10^{3a}$ | $2.4 \times 10^4$ |
| rAT | $1.9 \times 10^3$ | $2.5 \times 10^4$ |
| H-helix | | |
| AT-RK | $1.3 \times 10^2$ | $5.7 \times 10^3$ |
| AT-pos | $1.0 \times 10^3$ | $9.5 \times 10^3$ |
| AT-neut | $9.9 \times 10^2$ | $1.7 \times 10^4$ |
| AT-314R | $7.4 \times 10^2$ | $9.8 \times 10^3$ |
| Reactive site loop | | |
| AT-P3R | $2.6 \times 10^2$ | $1.0 \times 10^4$ |
| AT-rs1 | nd[b] | $6.1 \times 10^3$ |

[a]All $k_2$ values are in units of $M^{-1}$ $sec^{-1}$
[b]nd = below detectable limits Example 4

Role of the Reactive Site Loop Sequence of AT in the Inhibition of Thrombin

Inhibition in the Presence of Heparin. Protein C inhibitor has a higher affinity than AT for free thrombin in the absence of heparin. Heparin acceleration of thrombin inhibition is low with PCI compared with AT. The differences between AT and PCI inhibition of free thrombin has been assumed to be caused in part by a difference in the sequences of the reactive site loop. AT-rsl, AT-P3R, and wild-type AT all showed similar optimal heparin concentrations (FIG. 3). Heparin acceleration rates of the reactive site mutant proteins were also similar to wild-type AT (Table 5, FIG. 3).

Inhibition in the Presence of TM. Protein C inhibitor inhibits thrombin bound by thrombomodulin 140-fold better than free thrombin (Rezaie et al., 1995). Inhibition of thrombin bound by TM in the absence of chondroitin sulfate by PCI is similar to PCI inhibition of free thrombin. Binding to TM causes conformation changes in thrombin that may allow the reactive site loop of PCI to fit better than the reactive site loop of AT in the active site of thrombin. The rates of inhibition of TM-bound thrombin by the reactive site loop AT mutants were similar to the rate of inhibition by wild-type AT (Table 6).

Example 5

Role of the Reactive Site Loop Sequence of AT in the Inhibition of Other Serine Proteases Although AT does not inhibit APC, PCI inhibits APC ($k_2$=2.5×$10^4$ $M^{-1}s^{-1}$) at a rate similar to the inhibition of free thrombin ($k_2$=5×$10^5$ $M^{-1}s^{-1}$) (Cooper and Church, 1995; Pratt and Church, 1993; Shirk et al., 1994). The reactive site loop sequence may play a role in the difference between the rates of inhibition of APC by AT and PCI. However, AT-rsl and AT-P3R showed undetectable inhibition (<$10^2$ $M^{-1}s^{-1}$) of APC, similar to what was seen by AT (data not shown). Inhibition of trypsin by AT-rsl and AT-P3R showed little difference from the wild-type AT (Table 7).

Inhibition of Factor Xa by PCI is a very slow reaction (3.3×$10^4$ $M^{-1}s^{-1}$) (Cooper et al., 1995). Mutagenesis studies demonstrate that PCI with an arginine in the P3 position of its reactive site loop inhibits Factor Xa five fold more effectively than does wild-type PCI (Cooper et al., 1995). AT-rsl, which contains the reactive site loop sequence of PCI, had undetectable levels of inhibition of Factor Xa (Table 4). AT-P3R inhibited Factor Xa at a rate of 2.6×$10^2$ which was better than AT-rsl that showed undetectable levels of inhibition, but at a lower level than the wild-type rAT (1.9×$10^3$).

Example 6

Role of the H-helix of AT in Heparin Acceleration of Thrombin Inhibition

Although AT and PCI are similar in structure, their affinity for thrombin differs based on their amino acid sequences and the conformation of thrombin. Protein C inhibitor acts as a better inhibitor of free thrombin than AT. However, thrombin inhibition by AT increases (>300-fold) when heparin is used as a cofactor. Heparin only accelerates the reaction of PCI with thrombin 20- to 30-fold. When the H-helix of AT was mutated to a positive charge in mutant AT-pos to more closely resemble PCI, heparin acceleration of thrombin inhibition was reduced to only 34-fold, to a value similar to that of PCI (Table 5). By adding a new region of positive charges to the surface of AT, a new heparin binding site may be formed on AT. A new heparin binding site would provide a competitive binding site which decreases heparin binding to the pentasaccharide binding site on the D-helix, making the reactive site loop of AT more accessible to thrombin. Because the H-helix is positioned close to the reactive site loop of AT, changing the charge of that region would also directly affect interactions between AT and thrombin. Altering the charge at either end of the H-helix, mutants AT-RK and AT-314R, did not change heparin acceleration of thrombin inhibition.

Example 7

Role of the H-helix of AT in Thrombomodulin Acceleration of Thrombin Inhibition

When thrombin is bound by TM, its rate of inhibition by AT and PCI changes. Protein C inhibitor is a strong inhibitor of TM-bound thrombin. Antithrombin can inhibit TM-bound thrombin, but only when TM has chondroitin sulfate present as a cofactor. The rate of AT inhibition of thrombin with 4–6 TM, without chondroitin sulfate, is slightly less than that of free thrombin in the absence of heparin. All of the mutants, with the exception of AT-pos, inhibited thrombin bound to 4–6TM in a manner similar to wild-type AT. AT-pos showed a greater than 3-fold increase in inhibition when thrombin was bound to 4–6 TM (Table 6). The increase is probably due to protein-protein interactions between the thrombin and the H-helix of AT. The increase also may explain why PCI, with a positive H-helix, can inhibit TM-bound thrombin in the absence of a cofactor better than AT.

When RTM containing chondroitin sulfate was added to the reaction, the plasma and rAT showed a 3.1- and 28.0-fold increase in inhibition of thrombin, respectively. Mutant AT-pos showed a 90-fold increase in inhibition when thrombin was bound to the RTM, which was greater than the increase seen in the recombinant wild-type AT (Table 7). The chondroitin sulfate may be binding to the H-helix as an alternative binding site and drawing the AT-pos to the TM-bound thrombin. Alternatively, if the H-helix is playing a role in protein-protein interactions, the chondroitin sulfate may be binding to the D-helix of the AT and assisting in bridging the AT and thrombin together to increase the rate of inhibition.

By making the H-helix of AT positively charged, the activity of AT-pos does not resemble the anticoagulant activity of wild-type AT, but rather resembles the procoagulant activity seen in PCI (Elisen et al., 1998). While it can still inhibit free thrombin, the reaction that is usually accelerated by heparin does not occur at the same rate. Therefore, inhibition of free thrombin occurs at low levels regardless of the presence of heparin. When thrombin is bound to TM, thrombin activates protein C as part of a negative feedback mechanism to shut off thrombin production and slow down the coagulation cascade. AT-pos has a high inhibition rate of thrombin bound to 4–6 TM and the inhibition is accelerated even more when chondroitin sulfate is added as a cofactor on RTM. Inhibition of thrombin bound to TM shuts down the feedback mechanism and allows the production of more thrombin. By its decreased inhibition of free thrombin and increased inhibition of TM-bound thrombin, AT-pos has activity similar to PCI which acts as a procoagulant rather than an anticoagulant.

Example 8

Role of the Reactive Site Loop Sequence of AT in Thrombin Inhibition

Previous studies have focused on the role of the sequence of the reactive site loops of AT and PCI in inhibition of serine proteases (Cooper and Church, 1995; Cooper et al., 1995; Phillips et al., 1994; Stephens et al., 1988). These studies have shown that certain residues in the reactive site loop are crucial, and substituting other residues can alter the rate of inhibition of thrombin and other serine proteases. However, in this study, AT-rsl and AT-P3R, containing the reactive site loop sequences PCI and a PCI mutant, showed similar thrombin inhibition to wild-type AT. Both mutant proteins had only slightly lower levels of inhibition of free thrombin than the wild-type recombinant AT. They also showed similar degrees of heparin acceleration compared to the recombinant AT. These data suggest that the acceleration of inhibition by heparin is due mainly to conformational changes in the reactive site loop and the bridging effect of heparin rather than the binding of a specific amino acid sequence of the reactive site loop of the serpin to the active site of thrombin.

It was suggested that the reactive site loop sequence determined the specificity of inhibition when thrombin is bound to TM (Rezaie et al., 1995). Ironically, our reactive site loop mutants did not increase the inhibition of thrombin, suggesting that the reactive site loop sequence may play less of a role than other structural features in the reaction between thrombin and either AT or PCI.

Example 9

Role of the Reactive Site Loop Sequence of AT in Inhibition of Other Serine Proteases The reactive site loop sequence may also play less of a role in APC inhibition by AT. However, the reactive site loop sequence does seem to make a difference in the inhibition of Factor Xa by AT. Antithrombin inhibits Factor Xa ($k_2$=2.0×$10^3{}_M{}^{-1}s^{-1}$) less effectively than it does thrombin ($k_2$=6.6×$10^3{}_M{}^{-1}s^{-1}$) (Rezaie, 1998). The inhibition of Factor Xa by PCI is 1000-fold slower than AT inhibition of Factor Xa (Cooper et al., 1995). Mutant AT-rsl had an undetectable level of inhibition of Factor Xa, suggesting that it behaves like PCI in the reaction. Mutant AT-P3R showed a higher level of inhibition of Factor Xa than AT-rsl, but the level was still lower than that of the recombinant AT. This correlates with previous results in which PCI with an Arg substitution at the P3 position had a 5-fold better inhibition of Factor Xa than wild-type PCI, suggesting that the P3 residue plays a role in Factor Xa inhibition (Cooper et al., 1995).

Altering the sequence of the reactive site loop changed the rate of Factor Xa inhibition by AT, but the inhibition of APC, free thrombin, and thrombin bound to TM remained similar in AT containing either the reactive site loop sequence of AT or PCI. Changing the H-helix of AT into a positively-charged helix decreased the rate of inhibition of free thrombin in the presence of heparin and increased the rate of thrombin inhibition when TM was present. The charge of the H-helix appears to be a determining factor in inhibition of thrombin in the presence of heparin and TM, while the sequence of the reactive site loop seems to play less of a role.

Example 10

Extended Bioavailability of Factor VIII by Administration of AT-pos

As described above, AT-pos inhibits the protease activity of thrombin bound to thrombomodulin (T-TM). Inhibition of bound T-TM inhibits activation of protein C, which prevents activated protein C (APC) from degrading factor VIIIa. AT-pos thus exhibits procoagulant activity by inhibiting the degradation of factor VIIIa.

Treatment of Hemophilia A involves infusing patients with factor VIII. Patients with hemophilia A are deficient in factor VIII, but have the remaining clotting factors, so that during the normal activation and feedback pathways of the clotting cascade, factor VIII is degraded. Thus, repeated infusions of factor VIII are necessary. Administration of AT-pos to reduce the clearance rate and increase the bioavailability of the infused factor VIII is useful to improve treatment of hemophiliacs.

AT-pos inhibition of the APC-mediated feedback loop can be demonstrated in an animal model of hemophilia. For example, labeled factor VIII, full length or an active fragment thereof, is preferably labeled, for example, radiolabeled and co-administered to an animal with AT-pos. In one model, administration is by injection into the tail vein of BALB/c mice. At various time points, blood is collected from the injected animals and the assayed for bioavailable factor VIII, for example by monitoring the amount of radiolabeled factor VIII. The percentage of ligand remaining in circulation is calculated considering radioactivity of the aliquot taken at 1 minute after injection as 100%. Comparison of the bioavailability of factor VIII in animals also administered AT-pos is compared with control animals (no AT-pos) to demonstrate enhanced bioavailability provided by AT-pos.

Example 11

Treatment of Hemophilic Mice with AT-pos

Mice with targeted disruption of exons 16 or 17 of the factor VIII gene are genetically deficient in factor VIII. These animals exhibit less than 1% of the factor VIII activity of normal mice, impaired hemostasis, severe bleeding after minor injuries, subcutaneous and intramuscular bleeding after routine handling, and spontaneous bleeding (Bi et al., 1995; Bi et al., 1996; Wu et al., 2001), and are a model of hemophilia A.

Human factor VIII is administered to hemophilic mice via tail vein injection. AT-pos is co-administered to extend the bioavailability of the factor VIII. Control mice receive factor VIII but no AT-pos. At various time points after administration the animals are analyzed to determine the bioavailability of the factor VIII. For example, the mice are subjected to minor injuries such as tail cutting, and the time and/or extent of bleeding is determined (Turecek et al., 1997). Comparison of the bleeding in test animals administered AT-pos with control animals (no AT-pos) demonstrates the therapeutic activity of AT-pos.

This application contains numerous literature citations, each of which is hereby incorporated by reference for all purposes as if fully set forth.

While the invention is susceptible to various modifications and alternative forms, specific embodiments of the invention have been shown by way of the examples and are described in detail in the text above. It should be understood, however, that the description of the specific embodiments herein is not intended to limit the invention to the particular forms disclosed, but on the contrary, the intention is to cover all modifications, equivalents, and alternatives falling within the spirit and scope of the invention as defined by the appended claims.

REFERENCES

Bi, L., A. M. Lawler, S. F. Antonarakis, K. A. High, J. D. Gearhart, H. H. Kazazian. 1995. Targeted disruption of the mouse factor VIII gene produces a model of hemophilia A. *Nature Genet*, 10:119021.

Bi, L., R. Sarkar, T. Naas, A. M. Lawler, J. Pain, S. L. Shumaker, V. Bedian, H. H. Kazazian. 1996. Further characterization of factor VIII-deficient mice created by gene targeting: RNA and protein studies. *Blood*, 88:3446–50.

Bourin, M. C., M. C. Boffa, I. Bjork, and U. Lindahl. 1986. Functional domains of rabbit thrombomodulin. *Proc Natl Acad Sci USA*. 83:5924–8.

Bourin, M. C., A. K. Ohlin, D. A. Lane, J. Stenflo, and U. Lindahl. 1988. Relationship between anticoagulant activities and polyanionic properties of rabbit thrombomodulin. *J Biol Chem*. 263:8044–52.

Cooper, S. T., and F. C. Church. 1995. Reactive site mutants of recombinant protein C inhibitor. *Biochim Biophys Acta*. 1246:29–33.

Cooper, S. T., H. C. Whinna, T. P. Jackson, J. M. Boyd, and F. C. Church. 1995. Intermolecular interactions between protein C inhibitor and coagulation proteases. *Biochemistry*. 34:12991–7.

Danielsson, A., E. Raub, U. Lindahl, and I. Bjork. 1986. Role of ternary complexes, in which heparin binds both antithrombin and proteinase, in the acceleration of the reactions between antithrombin and thrombin or factor Xa. *J Biol Chem*. 261:15467–73.

Elisen, M. G., P. A. von dem Borne, B. N. Bouma, and J. C. Meijers. 1998. Protein C inhibitor acts as a procoagulant by inhibiting the thrombomodulin-induced activation of protein C in human plasma [published erratum appears in Blood 1998 Apr 15;91(8):3091]. *Blood*. 91:1542–7.

Ersdal-Badju, E., A. Lu, Y. Zuo, V. Picard, and S. C. Bock. 1997. Identification of the antithrombin III heparin binding site. *J Biol Chem*. 272:19393–400.

Gaffiey, P. J., T. A. Edgell, and C. M. Whitton. 1999. The haemostatic balance—Astrup revisited. *Haemostasis*. 29:58–71.

Gillespie, L. S., K. K. Hillesland, and D. J. Knauer. 1991. Expression of biologically active human antithrombin III by recombinant baculovirus in Spodoptera frugiperda cells. *J Biol Chem*. 266:3995–4001.

Hayashi, T., M. Zushi, S. Yamamoto, and K. Suzuki. 1990. Further localization of binding sites for thrombin and protein C in human thrombomodulin. *J Biol Chem*. 265:20156–9.

Huntington, J. A., and P. G. Gettins. 1998. Conformational conversion of antithrombin to a fully activated substrate of factor Xa without need for heparin. *Biochemistry*. 37:3272–7.

Jin, L., J. P. Abrahams, R. Skinner, M. Petitou, R. N. Pike, and R. W. Carrell. 1997. The anticoagulant activation of antithrombin by heparin. *Proc Natl Acad Sci USA*. 94:14683–8.

Lane, D. A., T. Bayston, R. J. Olds, A. C. Fitches, D. N. Cooper, D. S. Millar, K. Jochmans, D. J. Perry, K. Okajima, S. L. Thein, and J. Emmerich. 1997. Antithrombin mutation database: 2nd (1997) update. For the Plasma Coagulation Inhibitors Subcommittee of the Scientific and Standardization Committee of the International Society on Thrombosis and Haemostasis. *Thromb Haemost*. 77:197–211.

Le Bonniec, B. F., and C. T. Esmon. 1991. Glu-192—Gln substitution in thrombin mimics the catalytic switch induced by thrombomodulin. *Proc Natl Acad Sci USA*. 88:7371–5.

Mammen, E. F. 1998. Antithrombin: its physiological importance and role in DIC. *Semin Thromb Hemost*. 24:19–25.

Meagher, J. L., J. A. Huntington, B. Fan, and P. G. Gettins. 1996. Role of arginine 132 and lysine 133 in heparin binding to and activation of antithrombin. *J Biol Chem*. 271:29353–8.

Neese, L. L., C. W. Pratt, and F. C. Church. 1994. Modulation of protein C inhibitor activity. *Blood Coagul Fibrinolysis*. 5:737–46.

Neese, L. L., C. A. Wolfe, and F. C. Church. 1998. Contribution of basic residues of the D and H helices in heparin binding to protein C inhibitor. *Arch Biochem Biophys*. 355:101–8.

Olson, S. T., I. Bjork, R. Sheffer, P. A. Craig, J. D. Shore, and J. Choay. 1992. Role of the antithrombin-binding pentasaccharide in heparin acceleration of antithrombin-proteinase reactions. Resolution of the antithrombin conformational change contribution to heparin rate enhancement. *J Biol Chem*. 267:12528–38.

Olson, S. T., and J. D. Shore. 1982. Demonstration of a two-step reaction mechanism for inhibition of alpha-thrombin by antithrombin III and identification of the step affected by heparin. *J Biol Chem*. 257:14891–5.

Olson, S. T., A. W. Stephens, C. H. Hirs, P. E. Bock, and I. Bjork. 1995. Kinetic characterization of the proteinase binding defect in a reactive site variant of the serpin, antithrombin. Role of the P1' residue in transition-state stabilization of antithrombin-proteinase complex formation. *J Biol Chem*. 270:9717–24.

Phillips, J. E., S. T. Cooper, E. E. Potter, and F. C. Church. 1994. Mutagenesis of recombinant protein C inhibitor reactive site residues alters target proteinase specificity. *J Biol Chem*. 269:16696–700.

Potempa, J., E. Korzus, and J. Travis. 1994. The Serpin Superfamily of Proteinase Inhibitors: Structure, Function, and Regulation. *J Biol Chem*. 269:15957–15960.

Pratt, C. W., and F. C. Church. 1993. General features of the heparin-binding serpins antithrombin, heparin cofactor II and protein C inhibitor. *Blood Coagul Fibrinolysis*. 4:479–90.

Preissner, K. T., U. Delvos, and G. Muller-Berghaus. 1987. Binding of thrombin to thrombomodulin accelerates inhibition of the enzyme by antithrombin III. Evidence for a heparin-independent mechanism. *Biochemistry*. 26:2521–2528.

Prochownik, E. V., A. F. Markham, and S. H. Orkin. 1983. Isolation of a cDNA clone for human antithrombin III. *J Biol Chem*. 258:8389–8394.

Rezaie, A. R. 1997. Role of Leu99 of thrombin in determining the P2 specificity of serpins. *Biochemistry*. 36:7437–46.

Rezaie, A. R. 1998. Calcium enhances heparin catalysis of the antithrombin-Factor Xa reaction by a template mechanism. *J Biol Chem*. 273:16824–16827.

Rezaie, A. R., S. T. Cooper, F. C. Church, and C. T. Esmon. 1995. Protein C inhibitor is a potent inhibitor of the thrombin-thrombomodulin complex. *J Biol Chem*. 270:25336–9.

Rezaie, A. R., and C. T. Esmon. 1992. The function of calcium in protein C activation by thrombin and the thrombin-thrombomodulin complex can be distinguished by mutational analysis of protein C derivatives. *J Biol Chem.* 267:26104–9.

Roberts, H. R., and J. N. Lozier. 1992. New perspectives on the coagulation cascade. *Hosp Pract* (*Off Ed*). 27:97–105, 109–12.

Shirk, R. A., M. G. Elisen, J. C. Meijers, and F. C. Church. 1994. Role of the H helix in heparin binding to protein C inhibitor. *J Biol Chem.* 269:28690–5.

Stephens, A. W., A. Siddiqui, and C. H. Hirs. 1988. Site-directed mutagenesis of the reactive center (serine 394) of antithrombin III. *J Biol Chem.* 263:15849–52.

Turecek, P. L., H. Gritsch, G. Richter, W. Auer, L. Pichler, H. P. Schwarz. 1997. Assessment of bleeding for the evaluation of therapeutic preparations in small animal models of antibody-induced hemophilia and von willebrand disease. *Thromb Haemostas.* 77(3):591–9.

Weisel, J. W., C. Nagaswami, T. A. Young, and D. R. Light. 1996. The shape of thrombomodulin and interactions with thrombin as determined by electron microscopy. *J Biol Chem.* 271:31485–90.

Wu, H., M. Reading, J. Qian, D. K. Okita, E. Parker, P. Lollar, L. W. Hoyer, B. M. Conti-Fine. 2001. Mechanism of the immune response to human factor VIII in muring hemophilia A. *Thromb Haemost.* 85:125–33.

Ye, J., N. L. Esmon, C. T. Esmon, and A. E. Johnson. 1991. The active site of thrombin is altered upon binding to thrombomodulin. Two distinct structural changes are detected by fluorescence, but only one correlates with protein C activation. *J Biol Chem.* 266:23016–21.

We claim:

1. An isolated modified antithrombin protein having an H-helix, wherein at least one amino acid of the H-helix is substituted in order for the H-helix to have a more positive charge than an H-helix of a non-modified antithrombin protein.

2. The modified antithrombin protein of claim 1, wherein at least one negatively charged amino acid of the non-modified H-helix is substituted with a neutral or positively-charged amino acid to form the modified H-helix.

3. The modified antithrombin protein of claim 1, wherein at least one neutral amino acid of the non-modified H-helix is substituted with a positively-charged amino acid to form the modified H-helix.

4. The modified antithrombin protein of claim 1, wherein the at least one amino acid of the H-helix that is substituted in order for the H-helix to have a more positive charge than an H-helix of a non-modified antithrombin protein is in the region of amino acids 304–314 of the modified antithrombin protein.

5. The modified antithrombin protein of claim 4, wherein the modified antithrombin protein has one or more of the following amino acid substitutions: D309K, E310K, E312K, E313K, D309R, E310R, E312R, E313R.

6. The modified antithrombin protein of claim 5, wherein the modified antithrombin protein has the following amino acid substitutions: D309K, E310K, E312K, E313K.

7. A pharmaceutical composition comprising the modified antithrombin protein of claim 1 and a pharmaceutically acceptable carrier.

8. A pharmaceutical composition comprising the modified antithrombin protein of claim 5 and a pharmaceutically acceptable carrier.

9. A composition comprising the modified antithrombin protein of claim 1 and a therapeutically effective amount of Factor VIII.

10. The composition of claim 9, comprising a molar ratio of approximately 1:1 of said modified antithrombin to Factor VIII.

11. A method for treating a coagulation factor deficiency in a patient, comprising administering to said patient an effective inhibitory amount of the modified antithrombin protein of claim 1, wherein said inhibitory amount is effective to inhibit an actively of thrombin bound to thrombomodulin (T-TM).

12. The method of claim 11, wherein the inhibitory amount comprises a Protein C activation inhibitory amount of the modified antithrombin.

13. The method of claim 12, wherein the inhibitory amount comprises an amount of the modified antithrombin effective to inhibit Activated Protein C degradation of one or more of Coagulation Factors V, VIII, or X.

14. The method of claim 13, wherein the modified antithrombin has one or more amino acids in the region of amino acids 304–314 substituted in order to have a more positive charge than the non-modified antithrombin.

15. The method of claim 14, wherein the modified antithrombin has one or more of the following amino acid substitutions: D309K, E310K, E312K, E313K, D309R, E310R, E312R, E313R.

* * * * *

UNITED STATES PATENT AND TRADEMARK OFFICE

CERTIFICATE OF CORRECTION

PATENT NO. : 6,794,493 B2
DATED : September 21, 2004
INVENTOR(S) : Walston, Timothy et al.

It is certified that error appears in the above-identified patent and that said Letters Patent is hereby corrected as shown below:

<u>Column 1,</u>
Line 7, please insert the following:
-- STATEMENT REGARDING FEDERALLY SPONSORED RESEARCH AND DEVELOPMENT
This invention was made with United States government support awarded by the following agency: NIH HL58222-01. The United States has certain rights in this invention. --

Signed and Sealed this

Fourth Day of January, 2005

JON W. DUDAS
*Director of the United States Patent and Trademark Office*